US011844849B2

(12) United States Patent
Craig et al.

(10) Patent No.: US 11,844,849 B2
(45) Date of Patent: Dec. 19, 2023

(54) DENTAL COMPOSITIONS COMPRISING NANOPARTICLES PROVIDING A REFRACTIVE INDEX DIFFERENTIAL BETWEEN POLYMERIZABLE RESIN AND FILLER

(71) Applicant: 3M INNOVATIVE PROPERTIES COMPANY, St. Paul, MN (US)

(72) Inventors: Bradley D. Craig, Lake Elmo, MN (US); Timothy D. Dunbar, Woodbury, MN (US); Karsten Dede, Landsberg (DE); Adrian S. Eckert, Herrsching (DE); Ahmed S. Abuelyaman, Woodbury, MN (US); Gregory A. Kobussen, Woodbury, MN (US); Christoph H. Thalacker, Weilheim (DE); Paul J. Homnick, Lake Elmo, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/570,781

(22) Filed: Jan. 7, 2022

(65) Prior Publication Data

US 2022/0125687 A1 Apr. 28, 2022

Related U.S. Application Data

(63) Continuation of application No. 16/074,655, filed as application No. PCT/US2017/015928 on Feb. 1, 2017, now Pat. No. 11,246,808.

(60) Provisional application No. 62/291,661, filed on Feb. 5, 2016.

(51) Int. Cl.
| | |
|---|---|
| *A61K 6/80* | (2020.01) |
| *A61K 6/818* | (2020.01) |
| *A61K 6/16* | (2020.01) |
| *A61K 6/17* | (2020.01) |
| *A61K 6/71* | (2020.01) |
| *A61K 6/76* | (2020.01) |
| *A61K 6/78* | (2020.01) |
| *A61K 6/887* | (2020.01) |

(52) U.S. Cl.
CPC ............... *A61K 6/818* (2020.01); *A61K 6/16* (2020.01); *A61K 6/17* (2020.01); *A61K 6/71* (2020.01); *A61K 6/76* (2020.01); *A61K 6/78* (2020.01); *A61K 6/887* (2020.01)

(58) Field of Classification Search
CPC . A61K 6/818; A61K 6/16; A61K 6/17; A61K 6/71; A61K 6/76; A61K 6/78; A61K 6/887
See application file for complete search history.

(56) References Cited

U.S. PATENT DOCUMENTS

| | | | |
|---|---|---|---|
| 4,503,169 | A | 3/1985 | Randklev |
| 5,545,676 | A | 8/1996 | Palazzotto |
| 6,262,142 | B1 | 7/2001 | Wang |
| 6,284,898 | B1 | 9/2001 | Moszner |
| 6,387,981 | B1 | 5/2002 | Zhang |
| 6,572,693 | B1 | 6/2003 | Wu |
| 6,593,395 | B2 | 7/2003 | Angeletakis |
| 6,730,156 | B1 | 5/2004 | Windisch |
| 6,794,520 | B1 | 9/2004 | Moszner |
| 6,933,327 | B2 | 8/2005 | Yamakawa |
| 7,090,721 | B2 | 8/2006 | Craig |
| 7,090,722 | B2 | 8/2006 | Budd |
| 7,156,911 | B2 | 1/2007 | Kangas |
| 7,241,437 | B2 | 7/2007 | Davidson |
| 7,649,029 | B2 | 1/2010 | Kolb |
| 7,674,850 | B2 | 3/2010 | Karim |
| 8,476,338 | B2 | 7/2013 | Okubayashi |
| 8,647,510 | B2 | 2/2014 | Kolb |
| 8,710,113 | B2 | 4/2014 | Eckert |
| 8,722,759 | B2 | 5/2014 | Craig |
| 8,870,113 | B2 | 10/2014 | Kuo |
| 8,946,318 | B2 | 2/2015 | Akizumi |
| 9,056,043 | B2 | 6/2015 | Joly |
| 9,132,068 | B2 | 9/2015 | Toriyabe |

(Continued)

FOREIGN PATENT DOCUMENTS

| | | |
|---|---|---|
| DE | 19508586 | 9/1996 |
| DE | 202008018436 | 1/2014 |

(Continued)

OTHER PUBLICATIONS

Shortall, "Refractive index mismatch and monomer reactivity influence composite curing depth", J Dent Res, 2008, vol. 87, No. 1, pp. 84-88.

(Continued)

*Primary Examiner* — Sanza L. McClendon
(74) *Attorney, Agent, or Firm* — 3M Innovative Properties Company

(57) ABSTRACT

Dental compositions and methods of formulating a dental composition are described. In one embodiment, the dental composition comprises a polymerizable resin comprising one or more ethylenically unsaturated monomers or oligomers and nanoparticles. The nanoparticles have a refractive index of at least 1.600 and an average discrete or aggregate particle size of no greater than 100 nm. The dental composition further comprises inorganic metal oxide filler having a discrete or aggregate average particle size of at least 200 nm. The nanoparticles are present at a concentration to provide a refractive index differential between the cured polymerizable resin and inorganic metal oxide filler such that the contrast ratio of the dental composition is at least 40.

20 Claims, No Drawings

(56) References Cited

U.S. PATENT DOCUMENTS

| | | |
|---|---|---|
| 9,205,029 B2 | 12/2015 | Kalgutkar |
| 9,320,684 B2 | 4/2016 | Isizaka |
| 9,433,563 B2 | 9/2016 | Craig |
| 2002/0193462 A1 | 12/2002 | Angeletakis |
| 2005/0252413 A1 | 11/2005 | Kangas |
| 2005/0256223 A1 | 11/2005 | Kolb |
| 2006/0178469 A1 | 8/2006 | Moszner |
| 2008/0076847 A1 | 3/2008 | Moszner |
| 2008/0194722 A1 | 8/2008 | Abuelyaman |
| 2009/0298966 A1 | 12/2009 | Vanini |
| 2013/0003396 A1 | 1/2013 | Sakata |
| 2013/0203884 A1 | 8/2013 | Blomker |
| 2014/0099271 A1 | 4/2014 | Craig |
| 2014/0162216 A1 | 6/2014 | Craig |
| 2015/0094396 A1 | 4/2015 | Nakatsuka |
| 2015/0108694 A1 | 4/2015 | Shimosoyama |
| 2015/0272833 A1 | 10/2015 | Toriyabe |
| 2016/0008232 A1 | 1/2016 | Toriyabe |
| 2016/0081887 A1 | 3/2016 | Abuelyaman |

FOREIGN PATENT DOCUMENTS

| | | |
|---|---|---|
| EP | 1017354 | 7/2000 |
| EP | 1732499 | 12/2006 |
| EP | 2401998 | 1/2012 |
| EP | 2987480 | 2/2016 |
| JP | S63-218703 A | 9/1988 |
| JP | H2-206628 A | 8/1990 |
| JP | H7-196429 A | 8/1995 |
| WO | WO 2001-030304 | 5/2001 |
| WO | WO 2001-030305 | 5/2001 |
| WO | WO 2001-030306 | 5/2001 |
| WO | WO 2001-030307 | 5/2001 |
| WO | WO 2003-063804 | 8/2003 |
| WO | WO 2008-082881 | 7/2008 |
| WO | WO 2011-126647 | 10/2011 |
| WO | WO 2012-112304 | 8/2012 |
| WO | WO 2012-112350 | 8/2012 |
| WO | WO 2013/003396 | 1/2013 |
| WO | WO 2013/028397 | 2/2013 |
| WO | WO 2015-125470 | 8/2015 |

OTHER PUBLICATIONS

Ivoclar Vivadent, "Tetric Evoflow Bulk Fill, Tetric Evoceram Bulk Fill Frequently asked questions", 2015, pp. 01-14.

Watts, "Determination of Polymerization Shrinkage Kinetics in Visible-Light-Cured Materials: Methods Development", Dental Materials, 1991, vol. 7, No. 4, pp. 281-287.

Pallav, "Influence of Shearing Action of Food on Contact Stress and Subsequent Wear of Stress-bearing Composites", Journal of Dental Research, 1993, vol. 72, No. 1, pp. 56-61.

DENTAL COMPOSITIONS COMPRISING NANOPARTICLES PROVIDING A REFRACTIVE INDEX DIFFERENTIAL BETWEEN POLYMERIZABLE RESIN AND FILLER

CROSS REFERENCE TO RELATED APPLICATIONS

This application is a continuation of U.S. application Ser. No. 16/074,655, filed Aug. 1, 2018, now allowed, which is a national stage filing under 35 U.S.C. 371 of PCT/US2017/015928, filed Feb. 1, 2017, which claims priority to U.S. Provisional Application No. 62/291,661, filed Feb. 5, 2016, the disclosures of each of which are incorporated by reference herein in their entireties.

SUMMARY

Dental compositions typically comprise pigments to obtain the desired opacity (e.g. contrast ratio) and aesthetic shade. It has been found that the inclusion of pigments, especially titania, can hinder the depth of cure. Although various hardenable dental compositions have been described, industry would find advantage in compositions having improved properties such as a high depth of cure in combination with a high contrast ratio.

In one embodiment, a dental composition is described comprising a polymerizable resin comprising one or more ethylenically unsaturated monomers or oligomers and nanoparticles. The nanoparticles have a refractive index of at least 1.600 and an average discrete or aggregate particle size of no greater than 100 nm. The dental composition further comprises inorganic metal oxide filler having a discrete or aggregate average particle size of at least 200 nm. The nanoparticles are present at a concentration to provide a refractive index differential between the cured polymerizable resin inclusive of the nanoparticles and inorganic metal oxide filler such that the contrast ratio of the dental composition is at least 40.

In favored embodiments, the refractive index differential is balanced to maximize the contrast ratio, yet provide a depth of cure of at least 3.5 mm.

In another embodiment, a dental composition is described comprising a polymerizable resin comprising one or more ethylenically unsaturated monomers or oligomers wherein the polymerizable resin is substantially free of bisphenol-derived monomer. The polymerizable resin further comprises high refractive index nanoparticles as previously described. The concentration of components of the polymerizable resin and nanoparticles are selected such that the cured polymerizable resin inclusive of nanoparticles has a refractive index that differs from the (e.g. inorganic metal oxide) filler by at least 0.005, 0.006, 0.007, 0.008, 0.009, or 0.010.

In another embodiment, a dental composition is described comprising a polymerizable resin comprising at least one bisphenol-derived monomer and high refractive index nanoparticles (as just described). The concentration of components of the polymerizable resin and nanoparticles are selected such that the cured polymerizable resin inclusive of the nanoparticles has a refractive index that differs from the (e.g. inorganic metal oxide) filler by at least 0.010, 0.011, 0.012, 0.013, 0.014, or 0.015.

Also described are methods of treating a tooth surface, dental articles, and methods of making a dental composition.

DETAILED DESCRIPTION

The (hardenable) dental compositions described herein comprise a polymerizable resin and (e.g. inorganic metal oxide) filler.

The polymerizable resin is typically curable by exposure to actinic radiation (e.g. light) and therefore comprises at least one ethylenically unsaturated monomer or oligomer. In typical embodiments, such as dental composites, the polymerizable resin comprises at least one multifunctional ethylenically unsaturated monomer. The phrase "multifunctional ethylenically unsaturated" means that the monomers each comprise at least two ethylenically unsaturated (e.g. free radically) polymerizable groups. The ethylenically unsaturated group is typically a (e.g. terminal) free radically polymerizable group including (meth)acryl such as (meth)acrylamide ($H_2C=CHCON-$ and $H_2C=CH(CH_3)CON-$) and (meth)acrylate ($CH_2CHCOO-$ and $CH_2C(CH_3)COO-$). Other ethylenically unsaturated polymerizable groups include vinyl ($H_2C=C-$) including vinyl ethers ($H_2C=CHO-$). The ethylenically unsaturated terminal polymerizable group(s) is preferably a (meth)acrylate group, particularly for compositions that are hardened by exposure to actinic (e.g. UV or blue light) radiation. Further, methacrylate functionality is typically preferred over the acrylate functionality in curable dental compositions.

Various ethylenically unsaturated (e.g. (meth)acrylate) monomers for use in dental compositions are known in the art, several of which will subsequently be described.

The polymerizable resin further comprises (e.g. inorganic metal oxide) nanoparticles. Such nanoparticles, or in other words "nanoscopic fillers" can be used as viscosity and thixotropy modifiers. Such nanoparticles can also contribute in part to the mechanical properties of the hardenable dental composition. Due to their size, such nanoparticles also contribute to the refractive index of the polymerizable resin.

In some embodiments, the inorganic oxide nanoparticles have a primary particle size of no greater than 100 nm. The primary particle size typically refers to the size of a discrete, unaggregated particle. In other less common embodiments, the nanoparticle may be an aggregate of two or more (e.g. fused or covalently) bonded particles, wherein the aggregate has a particle size of no greater than 100 nm. The average particle size can be determined by cutting a thin sample of hardened dental composition and measuring the particle diameter of about 50-100 particles using a transmission electron micrograph at a magnification of 300,000 and calculating the average. The nanoparticles can have a unimodal or polymodal (e.g., bimodal) particle size distribution. In some embodiments, the (e.g. zirconia) nanoparticles have an average particle size of at least about 2, 3, 4, or 5 nanometers (nm). In some embodiments, the (e.g. zirconia) nanoparticles have an average particle size no greater than about 50, 40, 30, 25, 15, or 10 nanometers (nm).

In favored embodiments, the dental composition comprises (e.g. inorganic metal oxide) nanoparticles having a relatively high refractive index. The refractive index of the nanoparticles is typically greater than the refractive index of the individual organic components (e.g. (meth)acrylate monomers, etc.) as well as mixture of organic components of the polymerizable resin. Thus, the inclusion of the high refractive index nanoparticles can raise the refractive index of the polymerizable resin. In typical embodiments, high refractive index nanoparticles have a refractive index of at least 1.60, 1.65, 1.70, 1.75, 1.80, 1.85, 1.80, 1.85, or 2.00. Typical high refractive index inorganic metal oxide nanoparticles include alumina having a refractive index of 1.766, zirconia having a refractive index of 2.208, and titania having a refractive index of 2.614. In some embodiments, the nanoparticles can comprise a single inorganic oxide further comprising small amounts of other materials such as other metal oxides. For example, in some embodiments, the nanoparticles comprise zirconia and no greater than about 5 wt-% of other metal oxides, such as yttria. In other embodiments, the nanoparticles comprise appreciable amounts of more than one metal oxide such as a mixed metal oxide of zirconia and silica. In some embodiments, the inorganic metal oxide nanoparticles have a refractive index of no greater than 2.4 or 2.3, such as in the case of zirconia.

The dental composition optionally further comprises (e.g. inorganic metal oxide) nanoparticles having a relatively low refractive index, such as silica. The inclusion of the low refractive index nanoparticle can reduce the refractive index of the polymerizable resin. Suitable silica nanoparticles are commercially available from Ecolab (St. Paul, MN) under the product designation NALCO COLLOIDAL SILICAS. For example, preferred silica particles can be obtained from using NALCO products 1034A, 1040, 1042, 1050, 1060, 2327 and 2329.

Silica nanoparticles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Ecolab) and those which are low in sodium concentration and can be acidified by admixture with a suitable acid (e.g. Ludox colloidal silica made by E. I. Dupont de Nemours & Co. or Nalco 2326 from Ecolab).

In some embodiments, the dental composition comprises at least 0.5, 1, 1.5, or 2 wt.-% of low refractive index (e.g. silica) nanoparticles. The amount of low refractive index (e.g. silica) nanoparticles is typically no greater than 30, 25, 20, 15 or 5 wt.-% of the dental composition. In other embodiments, the dental composition comprise less than 1, 0.5, 0.25, 0.1, or 0.005 wt.-% of low refractive index (e.g. silica) nanoparticles or is substantially free of low refractive index (e.g. silica) nanoparticles.

When low refractive index (e.g. silica) nanoparticles are included in the dental composition, the concentration of low refractive index (e.g. silica) nanoparticles is generally less than the concentration of high refractive index (e.g. zirconia) nanoparticles. Thus, the weight or volume concentration of high refractive index (e.g. zirconia) nanoparticles is typically greater than the weight or volume concentration of low refractive index (e.g. silica) nanoparticles. In some embodiments, the weight or volume ratio of high refractive index (e.g. zirconia) nanoparticles to low refractive index (e.g. silica) nanoparticles is at least 1.1 to 1, 1.2 to 1, 1.3 to 1, 1.4 to 1, 1.5 to 1, 1.6 to 1, 1.7 to 1, 1.8 to 1, 1.9 to 1, or 2 to 1. In some embodiments, the weight or volume ratio of high refractive index (e.g. zirconia) nanoparticles to low refractive index (e.g. silica) nanoparticles is at least 2.1 to 1, 2.2 to 1, 2.3 to 1, or 2.4 to 1. In some embodiments, the weight or volume ratio of high refractive index (e.g. zirconia) nanoparticles to low refractive index (e.g. silica) nanoparticles is no greater than 100 to 1, 75 to 1, 50 to 1, 25 to 1, 10 to 1, or 5 to 1.

Some suitable low refractive index (e.g. silica) nanoparticles and high refractive index (e.g. zirconia) nanoparticles are disclosed in U.S. Pat. No. 6,387,981 (Zhang et al.) and U.S. Pat. No. 6,572,693 (Wu et al.) as well as PCT International Publication Nos. WO 01/30304 (Zhang et al.), WO 01/30305 (Zhang et al.), WO 01/30307 (Zhang et al.), WO 03/063804 (Wu et al.), U.S. Pat. No. 7,090,721 (Craig et al.), U.S. Pat. No. 7,090,722 (Budd et al.), U.S. Pat. No. 7,156,911 (Kangas et al.), U.S. Pat. No. 7,241,437 (Davidson et al.) and U.S. Pat. No. 7,649,029 (Kolb et al.).

The dental compositions described herein preferably comprise appreciable amounts of inorganic metal oxide filler. Fillers used in dental applications are typically ceramic in nature.

Fillers may be selected from one or more of a wide variety of materials suitable for incorporation in compositions used for dental applications, such as fillers currently used in dental composites and dental (e.g. crown) articles, and the like. The filler is generally non-toxic and suitable for use in the mouth. The filler can be radiopaque, radiolucent, or nonradiopaque. In some embodiments, the filler typically has a refractive index of at least 1.500, 1.510, 1.520, 1.530, or 1.540.

It is common to include up to about 5 wt-% of a component, such as $YbF_3$ to increase the radiopacity. In some embodiments, the radiopacity of the cured dental composition is at least 3 mm thickness of aluminum.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

The dental compositions described herein comprise inorganic metal oxide filler material that is larger in size than the nanoparticles. As previously described, the nanoparticles are typically discrete, unaggregated particles having a particle size of no greater than 100 nm. In contrast, the inorganic metal oxide filler is a particulate or fibrous material having at least one dimension greater than 100 nm such as at least 150 nm or at least 200 nm. In the case of particulate fillers, the average particle size of a discrete unaggregated particle or an aggregated particle is at least 200 nm. Inorganic metal oxide filler particles are very effective for improving post-cure wear properties.

In some embodiments, the cured dental composition exhibits a flexural strength of at least 120, 130, or 140 MPa and typically no greater than 200 MPa or 250 MPa. In some embodiments, the cured dental composition exhibits a flexural modulus of at least 3, 4, 5, 6, 7, 8, 9, or 10 GPa and typically no greater than 15 or 20 GPa.

In some embodiments, the filler can comprise crosslinked organic material that is insoluble in the polymerizable resin, and may optionally be filled with inorganic filler. Examples of suitable organic filler particles include filled or unfilled pulverized polycarbonates, polyepoxides, poly(meth)acrylates and the like.

In some embodiments, the dental compositions described herein comprises acid-reactive fillers, provided that the dental composition does not comprise a component, such as a carboxylate, that reacts with the acid-reactive filler to an appreciable extent. Acid-reactive metal oxide fillers include for example barium oxide, calcium oxide, magnesium oxide, and zinc oxide. Acid-reactive glasses include borate glasses, phosphate glasses, and fluoroaluminosilicate ("FAS") glasses. However, in typical embodiments, the dental composition comprises non-acid reactive fillers and the dental composition is substantially free (less than 1, 0.5, 0.25, 0.1, or 0.005 wt.-%) of acid-reactive fillers.

In some embodiments, the dental compositions described herein comprises non-acid-reactive fillers such as quartz, fumed silica, non-vitreous microparticles of the type described in U.S. Pat. No. 4,503,169 (Randklev), as well as nanocluster fillers, such as described in U.S. Pat. No. 6,730,156 (Windisch et al.), U.S. Pat. No. 6,572,693 (Wu et al.), and U.S. Pat. No. 8,722,759 (Craig).

In some embodiments, the filler comprises nanoparticles in the form of nanoclusters, i.e. a group of two or more particles associated by relatively weak, but sufficient intermolecular forces that cause the particles to clump together, even when dispersed in a hardenable resin. Preferred nanoclusters can comprise a loosely aggregated substantially amorphous cluster of non-heavy metal oxide (e.g. silica) particles, and heavy metal oxide (i.e. having an atomic number greater than 28) such as zirconia. The zirconia can be crystalline or amorphous. In some embodiments, the zirconia may be present as a particle. The particles from which the nanocluster is formed preferably have an average diameter of less than about 100 nm. However, the average particle size of the loosely aggregated nanocluster is typically considerably larger.

Mixtures of fillers can also be used. When a mixture of filler is used, a sufficient amount of the filler has a different refractive index than the cured polymerizable resin, inclusive of nanoparticles to provide the contrast ratio as described herein. In some embodiments, at least 40, 50, 60, 70, 80, 90 wt-% or greater of the total mixture of filler is filler having a different refractive index than the cured polymerizable resin inclusive of the nanoparticles. Thus, a portion of the filler can be a filler that has the same or more similar refractive index than the cured polymerizable resin.

In some embodiments, the dental compositions described herein comprise at least 60, 61, 62, 63, 64, or 65 wt-% of nanocluster filler based on the total weight of the composition. The maximum amount of nanocluster filler is typically no greater than 75% or 80%. In some embodiments, the total amount of inorganic metal oxide material (i.e. nanoparticle and filler) is at least 70, 71, 72, 73, 74, or 75 wt.-%. The maximum amount of inorganic metal oxide material (i.e. nanoparticle and filler) is typically no greater than 80% or 85%.

In some embodiments, the (e.g. nanocluster) filler particle has a higher refractive index than the organic phase of the polymerizable resin. For example, the (e.g. nanocluster) filler particle may have a refractive index of at least 1.530, 1.535, or 1.540; whereas the organic phase (i.e. in the absence of nanoparticles) of the polymerizable resin has a refractive index of 1.500, 1.505, 1.510, 1.515, 1.520, 1.525.

Due to the size of the filler, the filler does not raise the refractive index of the polymerizable resin. Rather, with regard to refractive index, the filler acts as a separate phase.

In some embodiments, the dental composition comprises a sufficient amount of high refractive index (e.g. zirconia) nanoparticles to provide a refractive index differential between the cured polymerizable resin (i.e. inclusive of the nanoparticles) and the inorganic metal oxide filler such that the contrast ratio is at least 40, 41, 42, 43, 44, or 45.

As the concentration of high refractive index (e.g. zirconia) nanoparticles increases, the refractive index differential between the cured polymerizable resin inclusive of the nanoparticles and the filler can increase thereby providing a contrast ratio (opacity) increase. However, even in the absence of (e.g. titania) pigment particles, the depth of cure decreases with increasing contrast ratio (e.g. opacity). Thus, the concentration of components of the polymerizable resin and nanoparticles are selected to provide a synergistic balance of contrast ratio and depth of cure. In some embodiments, the refractive index differential and contrast ratio is maximized for a depth of cure of at least 3.5 mm or 4 mm.

The refractive index differential that can provide a contrast ratio of at least 40 can vary depending on the polymerizable resin composition. In typical embodiments, the refractive index differential is at least 0.005, 0.006, 0.007, 0.008, 0.009 and is some embodiments at least 0.010, 0.011, 0.012, or 0.013 even in the absence of (e.g. titania) pigments.

In some embodiments, such as in the case of dental compositions comprising little or no bisphenol-derived monomers, the refractive index differential may be no greater than 0.025, 0.024, 0.023, 0.021, or 0.020. In other embodiments, such as in the case of dental compositions comprising appreciable amounts of bisphenol-derived monomers, the refractive index differential may be no greater than 0.055, 0.054, 0.053, 0.052, 0.051, 0.050, 0.049, 0.048, 0.047, 0.046, or 0.045. When the differential is too high, the depth of cure even in the absence of (e.g. titania) pigment, can disadvantageously be less than 3.5 mm (or in other words 4 mm according to the ISO 4049 standard).

In some embodiments, the refractive index of the uncured polymerizable resin inclusive of nanoparticles is less than the refractive index of the filler. In other embodiments, the refractive index of the uncured polymerizable resin inclusive of nanoparticles is equal to or greater than the refractive index of the filler. In typical embodiments, the refractive index of the cured polymerizable resin inclusive of nanoparticles is greater than the refractive index of the filler. In some embodiments, the refractive index of the filler is between (such as the midpoint) the uncured polymerizable resin inclusive of nanoparticles and the cured polymerizable resin inclusive of nanoparticles.

Since the contrast ratio is provided by the refractive index differential between the cured polymerizable resin (i.e. inclusive of the nanoparticles) and the inorganic metal oxide filler, such contrast ratio can be provided in the absence of pigments and at lower pigment concentrations. The pigment concentration can also vary depending on the polymerizable resin composition. Pigment particles typically having a discrete or aggregate particle size of at least 150 nm.

In some embodiments, such as in the case of dental compositions comprising little or no bisphenol-derived based monomers, the dental composition may comprise no greater than 0.05, 0.04, or 0.03 wt.-% of pigment particles such as high refractive index (e.g. titania) pigment particles. In other embodiments, such as in the case of dental compositions comprising appreciable amounts of bisphenol-derived based monomers, the dental composition may comprise no greater than 0.07, 0.06, or 0.05 wt.-% of the pigment particles such as high refractive index (e.g. titania) pigment particles.

In some embodiments, such as in the case of dental compositions comprising little or no bisphenol-derived based monomers, the contrast ratio (even in the absence of (e.g. titania) pigment) is typically no greater than 60, 59, 58, 57, 56, 55. In other embodiments, such as in the case of dental compositions comprising appreciable amounts of bisphenol-derived based monomers, the contrast ratio (even in the absence of (e.g. titania) pigment) is typically no greater than 70, 69, 68, 67, 66, 65, 64, 63, 62, 61, 60, 59, 58, 57, 56, or 55.

In some embodiments, such as in the case of dental compositions comprising little or no bisphenol-derived based monomers, the dental composition typically comprises at least 2, 2.5, 3, 3.5, or 4 wt.-% of high refractive index (e.g. zirconia) nanoparticles. The amount of high refractive index (e.g. zirconia) nanoparticles is typically no greater than 20, 19, 18, 17, 16, 15, 14, 13, 12, 11, or 10 wt.-% of the dental composition.

In other embodiments, such as in the case of dental compositions comprising appreciable amounts of bisphenol-derived based monomers, the dental composition typically comprises at least 4.5, 5, 5.5, 6, 6.5, 7, 7.5, 8, 8.5, 9, 9.5 or 10 wt.-% of high refractive index (e.g. zirconia) nanoparticles. The amount of high refractive index (e.g. zirconia) nanoparticles is typically no greater than 20, 19, 18, 17, 16, 15, 14, 13, 12, 11, or 10 wt.-% of the dental composition.

The concentration of high refractive index nanoparticles just described is preferred for zirconia. When the high refractive index nanoparticles have a higher refractive index than zirconia, such as in the case of titania, lower concentrations of nanoparticles would be employed. Further, when the high refractive index nanoparticles have a lower refractive index than zirconia, such as in the case of alumina, higher concentrations of nanoparticles would be employed.

In typical embodiments, the (e.g. high refractive index) inorganic metal oxide nanoparticles and inorganic oxide filler comprise a surface treatment to enhance the bond between the nanoparticles and inorganic oxide filler and the resin. Various surface treatments have been described in the art including for example organometallic coupling agents and carboxylic acids such as described in U.S. Pat. No. 8,647,510 (Davidson et al.)

Suitable copolymerizable organometallic compounds may have the general formulas: $CH_2=C(CH_3)_mSi(OR)_n$ or $CH_2=C(CH_3)_mC=OOASi(OR)_n$; wherein m is 0 or 1, R is an alkyl group having 1 to 4 carbon atoms, A is a divalent organic linking group, and n is from 1 to 3. The organometallic coupling agent may be functionalized with reactive curing groups, such as acrylates, methacrylates, vinyl groups and the like. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependent upon several factors such as particle size, particle type, modifier molecular weight, and modifier type. In general it is preferred that approximately a monolayer of modifier is attached to the surface of the particle.

It is known that the refractive index of a mixture of components can be calculated by determining the sum of the refractive index of each component multiplied by the volumetric fraction of such component in the mixture. The equation is as follows:

$$N_{material} = \sum_{i=1}^{n} N_i V_i$$

wherein $N_i$ is the refractive index of a given component, i; $V_i$ is the volume fraction of the given component, i; and n is the number of components.

As appreciated by one of ordinary skill in the art, although all the components can be utilized in the calculation, it is generally sufficient to utilize all the polymerizable (e.g. monomer and oligomer) components and the nanoparticles. The volume of a material can be calculated from a known mass and density of the material. Further, if the refractive index of the mixture is known and the volumes of the components are known, an unknown refractive index of a material of a known volume in a mixture may be calculated through the same equation provided that the refractive index of the other components are known.

The amount of surface treatment with respect to total volume of filler is generally relatively small such that the presence of the surface treatment has a negligible effect of the refractive index of the filler. Other components that generally have a negligible effect include initiators and additives. However, in the case of the nanoparticles, the amount of surface treatment with respect to the total volume of inorganic metal oxide nanoparticles is of significance and is included in the calculation.

The refractive index and density of various components commonly utilized in hardenable dental compositions is reported in the literature or provided by the supplier of such material. For components that are not reported in the literature, density and refractive index values can be measured using known and established techniques. For example, mercury porosimetry can be used for determination of density and the refractive index can be measured according to the methods described in the forthcoming examples. The refractive index and density of some representative components are as follows:

TABLE A

| Material | Refractive index | Density (g/cm³) |
| --- | --- | --- |
| BisGMA | 1.55 | 1.161 |
| ERGP-IEM | 1.541 | 1.21 |
| TEGDMA | 1.461 | 1.072 (literature) |
| UDMA | 1.483 | 1.129 |
| DDDMA | 1.455 | 0.95 |
| AFM-1 | 1.4868 | 1.16 |
| Surface Treated Nanozirconia | 1.689 (calculated) | 3.371 |
| GF-31 | 1.431 (literature) | 1.045 (literature) |
| Surface Treated Silica/Zirconia Clusters | 1.538 (calculated) | Not tested |
| Surface Treated 20 nm Silica | 1.454 (calculated) | 2.091 |

Hence the calculated refractive index of an uncured polymerizable resin inclusive of the nanoparticles can be calculated.

In some embodiments, the refractive index of the uncured polymerizable resin inclusive of the surface modified nanoparticles differs from the refractive index of the inorganic oxide filler by an amount greater than 0.020. For example, the difference may be at least 0.021, 0.022, or 0.023. In other embodiments, the refractive index of the uncured polymerizable resin inclusive of the (e.g. surface modified nanoparticles) differs from the refractive index of the inorganic oxide filler, by an amount no greater than 0.020. In some embodiments, the refractive index of the uncured polymerizable resin inclusive of the surface modified nanoparticles differs from the refractive index of the inorganic oxide filler by at least 0.015, 0.016, 0.017, 0.018, 0.019.

As can be determined by one or ordinary skill in the art, the uncured polymerizable resin generally increases in refractive index by a magnitude of about 0.030 to about 0.040 depending of the densification (shrinkage) of the polymerizable monomers. Thus, the refractive index of the cured polymerizable resin can be approximated from the calculated uncured polymerizable resin and vice-versa.

In one embodiment, a method of formulating a dental composition is described comprising providing the refractive index one or more ethylenically unsaturated monomers of a polymerizable resin; providing the refractive index of at least one filler; calculating the refractive index of the polymerizable resin and filler; adjusting the refractive index of the polymerizable resin with nanoparticles to obtain a sufficient refractive index differential (as previously described) such that the cured dental composition has a contrast ratio of at least 40. Hence, this method can be used to "design" a dental composition with the desired refractive index properties and thus, contrast ratio.

In one embodiment, the polymerizable resin (inclusive of the surface modified nanoparticles) is designed such that prior to curing the refractive index is less than the filler and after curing is greater than the refractive index of the filler. Without intending to be bound by theory, it is surmised that such polymerizable resin (inclusive of the surface modified nanoparticles) increases in transparency while curing as the refractive index approaches that of the filler. This contributes to the high depth of cure. Further, the same polymerizable resin (inclusive of the surface modified nanoparticles) decreases in transparency and increases in contrast ratio during curing as the refractive index of the polymerizable resin (inclusive of nanoparticles) surpasses the refractive index of the filler. In some embodiments, the polymerizable resin (inclusive of the surface modified nanoparticles) is designed such that the refractive index of the filler is near the midpoint between the uncured and cured refractive index of the polymerizable resin (inclusive of nanoparticles).

Various ethylenically unsaturated monomers can be utilized in the dental composition. The ethylenically unsaturated monomers of the dental composition are typically stable liquids at about 25° C. meaning that the monomer do not substantially polymerize, crystallize, or otherwise solidify when stored at room temperature (about 25° C.) for a typical shelf life of at least 30, 60, or 90 days. The viscosity of the monomers typically does not change (e.g. increase) by more than 10% of the initial viscosity.

Particularly for dental restoration compositions, the ethylenically unsaturated monomers generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight monomer lacking such substituents).

In typical embodiments, the polymerizable resin comprises at least one monomer comprising at least two ethylenically unsaturated (e.g. (meth)acrylate) groups such as a bisphenol-derived monomer, an (e.g. aromatic) low volume shrinkage resin, or a combination thereof.

Preferred dental compositions described herein comprise one or more low volume shrinkage monomers such that the composition exhibits a Watts Shrinkage of less than about 2%. In some embodiments, the Watts Shrinkage is no greater than 1.90%, or no greater than 1.80%, or no greater than 1.70%, or no greater than 1.60%.

Low volume shrinkage monomers include the compounds described in U.S. Pat. No. 8,710,113; isocyanurate monomers, such as described in WO2011/126647; tricyclodecane monomers, such as described in EP Application No. 10168240.9, filed Jul. 2, 2010; polymerizable compounds having at least one cyclic allylic sulfide moiety such as described in US2008/0194722; methylene dithiepane silanes as described in U.S. Pat. No. 6,794,520; oxetane silanes such as described in U.S. Pat. No. 6,284,898; and di-, tri, and/or tetra-(meth)acryloyl-containing materials such as described in WO2008/082881; each of which are incorporated herein by reference.

In some favored embodiments, the majority of the (e.g. unfilled) polymerizable resin composition comprises one or more low volume shrinkage monomers. For example, at least 50%, 60%, 70%, 80%, 90% or more of the (e.g. unfilled) polymerizable resin may comprise low volume shrinkage monomer(s).

In one embodiment, dental composition described a low volume shrinkage monomer as described in U.S. Pat. No. 8,710,113. Such monomers contain a single backbone unit (U) with 6 to 20 carbon atoms, at least 6 carbon atoms thereof forming an aromatic or an aliphatic cyclic moiety, the remaining carbon atoms either being part of substituents pending from the cyclic moiety or being part of bridging groups to spacer units, wherein one or more of the remaining carbon atoms can be replaced by an oxygen atom. The backbone unit typically does not comprise a bisphenol structure and preferably comprises no halogen atoms (e.g. F, Cl, Br).

The monomers further comprise one or two unit(s) (S) being connected to the backbone unit (U) via an ether linkage, at least one spacer unit (S) comprising a —CH2-CH2-CH2-CH2-O—CH2-CH(Q)-OG chain or a —CH2-CH(OG)—CH2-OM residue or a mixture of these two types of spacers within one spacer unit, wherein G is bonded to the spacer unit(s) (S) via an urethane moiety, each group G comprising at least one polymerizable moiety, M comprises at least one group selected from acryloyl, methacryloyl, aryl, mixtures and combinations thereof, and Q comprises at least one group selected from hydrogen, methyl, phenyl, phenoxymethyl, mixtures and combinations thereof. At least two G groups are present in such a compound. Further, where there is only one unit (S) is present, the G group is not part of said unit (S) is located in a substituent pending from unit (U) that has two substituents, each bearing a group G.

In some embodiments, the backbone unit (U) may comprise a moiety selected from

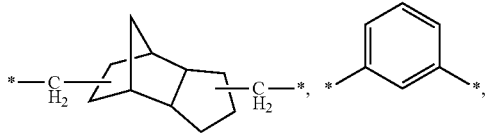

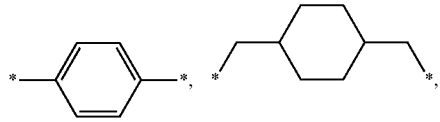

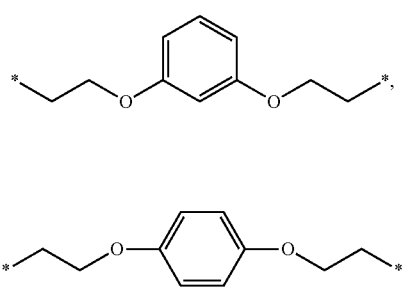

The polymerizable moiety G may comprise a moiety selected from

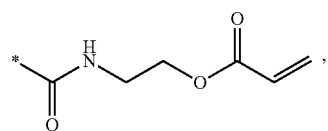

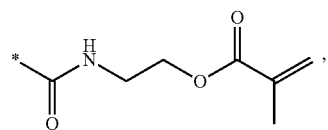

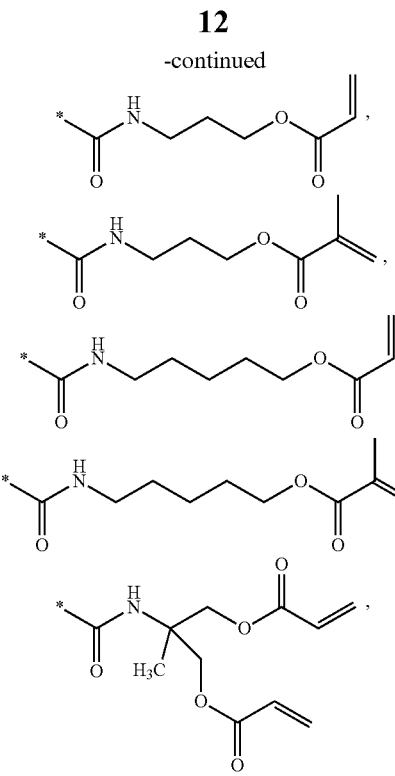

and combinations thereof.

Various representative structures are described in U.S. Pat. No. 8,870,113. One of such compounds is as follows:

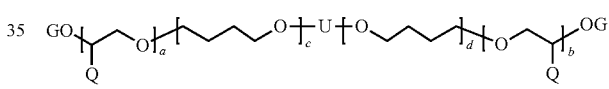

wherein Q=hydrogen, methyl, phenyl or phenoxymethyl,
a, b, c and d=0 to 3,
(a+b)=1 to 6, and
(c+d)=1 to 6.

Another compound is as follows, wherein U and G are as defined above.

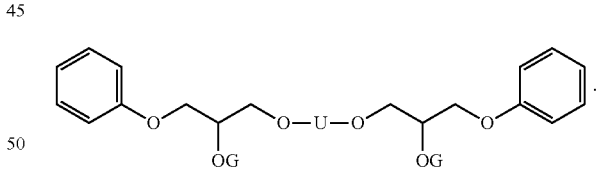

One representative compound is as follows:

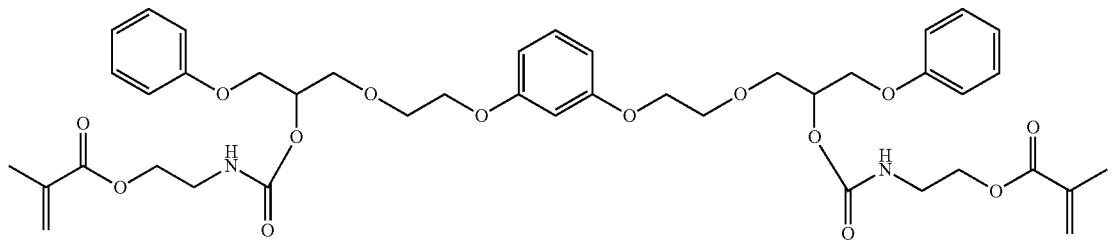 [SMILES: C=C(C)C(=O)OCCNC(=O)OC(COCCOc1cccc(OCCOCC(COc2ccccc2)OC(=O)NCCOC(=O)C(=C)C)c1)COc1ccccc1]

The linking groups of the low shrinkage monomers are typically sufficiently low in molecular weight such that the monomer is a stable liquid at 25° C. However, the linking group(s) is typically higher in molecular weight than the oxygen atom of for example 2,2-bis[4-(2-hydroxy-3-methacryloyloxypropoxy)phenyl]propane ("BisGMA"), a common monomer utilized in dental compositions, that links the (meth)acrylate group to the aromatic ring. The molecular weight of the linking group(s) of the monomers described is typically at least 50 g/mole or 100 g/mole. In some embodiments, the molecular weight of the linking group is at least 150 g/mole. The molecular weight of the linking group is typically no greater than about 500 g/mole. In some embodiments, the molecular weight of the linking group is no greater than 400 g/mole or 300 g/mole.

In some embodiments, the (i.e. calculated) molecular weight of the low monomers is typically no greater than 2000 g/mole. In some embodiments, the molecular weight of the monomers is no greater than about 1500 g/mole or 1200 g/mole or 1000 g/mole. The molecular weight of the monomers is typically at least 600 g/mole.

Increasing the molecular weight without forming a solid at 25° C. can be achieved by various synthetic approaches. In some embodiments, the monomers have one or more pendant (e.g. polymerizable) substituents. In other embodiments, the monomers comprise at least one aliphatic cyclic moiety and/or comprise one or more aromatic moieties.

The multifunctional low shrink monomers are (e.g. highly) viscous liquids at about 25° C., yet are flowable. The viscosity as can be measured with a Haake RotoVisco RV1 device, as described in EP Application No. 10168240.9, filed Jul. 2, 2010; is typically at least 300, or 400, or 500 Pa*s and no greater than 10,000 Pa*s. In some embodiments, the viscosity is no greater than 5000 or 2500 Pa*s.

In some embodiments, the dental composition comprises at least 5 wt-%, 10 wt-%, or 15 wt-% and typically no greater than 30 wt-%, 25 wt-%, or 20 wt-% of low volume shrinkage monomer. Mixtures of low volume shrinkage monomers can be improved, some of which are exemplified in WO 2012/112350; incorporated herein by reference.

In other embodiments, the polymerizable resin comprises a bisphenol-derived monomer such as ethoxylated bisphenol A dimethacrylate (BisEMA6), bisphenol A diglycidyl dimethacrylate (bisGMA), and mixtures thereof. In this embodiment, the dental composition comprises at least 5 wt-%, 10 wt-%, or 15 wt-% and typically no greater than 30 wt-%, 25 wt-%, or 20 wt-% of bisphenol-derived monomer.

In some embodiments, the dental composition further comprises a low viscosity reactive (i.e. polymerizable) diluent. Reactive diluents typically have a viscosity as can be measured with a Haake RotoVisco RV1 device, as described in EP Application No. 10168240.9, filed Jul. 2, 2010, of no greater than 300 Pa*s and preferably no greater than 100 Pa*s, or 50 Pa*s, or 10 Pa*s. In some embodiments, the reactive diluent has a viscosity no greater than 1 or 0.5 Pa*s. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono(meth)acrylate or di(meth)acrylate monomers.

Some representative reactive diluents include 1,12-dodecanediol dimethacrylate (DDDMA), urethane dimethacrylate (UDMA), triethlyene glycol dimethacrylate (TEGDMA), glycerol dimethacrylate (GDMA), ethyleneglycol dimethacrylate, neopentylglycol dimethacrylate (NPGDMA), and polyethyleneglycol dimethacrylate (PEGDMA).

Various mixtures of reactive diluents can be utilized. In some embodiments, the dental composition comprises at least 0.5, 1 or 2 wt.-% of reactive diluent(s). Typically the concentration of reactive diluent(s) is no greater than 10, 9, 8, or 7 wt.-% of the total dental composition.

In some embodiments, the dental composition comprises at least one addition-fragmentation agent. The addition-fragmentation agent comprises at least one ethylenically unsaturated terminal group and a backbone unit comprising an α, β-unsaturated carbonyl. The addition-fragmentation agent is free-radically cleavable.

The addition-fragmentation agents are preferably of the following formula:

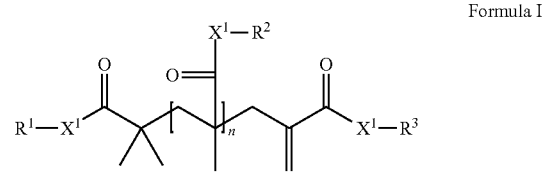

Formula I wherein
$R^1$, $R^2$ and $R^3$ are each independently $Z_m$-Q-, a (hetero) alkyl group or a (hetero)aryl group with the proviso that at least one of $R^1$, $R^2$ and $R^3$ is $Z_m$-Q-,
Q is a linking group have a valence of m+1;
Z is an ethylenically unsaturated polymerizable group,
m is 1 to 6, preferably 1 to 2;
each $X^1$ is independently —O— or —NR$^4$—, where $R^4$ is H or $C_1$-$C_4$ alkyl, and n is 0 or 1.

Addition-fragmentation agents according to Formula I are described in U.S. Pat. No. 9,056,043; incorporated herein by reference.

In a favored embodiment, the addition-fragmentation material ("AFM") is added to a dental composition comprising at least one ethylenically unsaturated monomer or oligomer. Without intending to be bound by theory, it is surmised that the inclusion of such addition-fragmentation material reduces the polymerization-induced stresses, such as by the mechanism described in PCT Publication WO 2012/112304. For embodiments wherein the AFM are multifunctional, comprising at least two ethylenically unsaturated group (e.g. Z is ≥2 in Formula I), the material can function as crosslinking agents, where the crosslinks are labile.

The ethylenically unsaturated moiety, Z, of the monomer may include, but is not limited to the following structures, including (meth)acryloyl, vinyl, styrenic and ethynyl, that are more fully described in reference to the preparation of the compounds below.

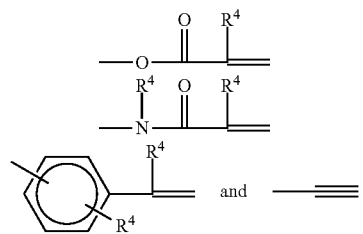

wherein $R^4$ is H or $C_1$-$C_4$ alkyl.

In some embodiments, Q is selected from —O—, —S—, —NR$^4$—, —SO$_2$—, —PO$_2$—, —CO—, —OCO—, —R$^6$—, —NR$^4$—CO—NR$^4$—, NR$^4$—CO—O—, NR$^4$—CO—NR$^4$—CO—O—R$^6$—, —CO—NR$^4$—R$^6$—, —R$^6$—CO—O—R$^6$—, —O—R$^6$. —S—R$^6$—, —NR$^4$—R$^6$—, —SO$_2$—R$^6$—, —PO$_2$—R$^6$—, —CO—R$^6$—, —OCO—R$^6$—, —NR$^4$—CO—R$^6$—, NR$^4$—R$^6$—CO—O—, and NR$^4$—CO—NR$^4$—, wherein each R$^4$ is hydrogen, a C$_1$ to C$_4$ alkyl group, or aryl group, each R$^6$ is an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

In some embodiments, Q is an alkylene, such as of the formula —C$_r$H$_{2r}$—, where r is 1 to 10. In other embodiments, Q is a hydroxyl-substituted alkylene, such as —CH$_2$—CH(OH)—CH$_2$—. In some embodiments, Q is an aryloxy-substituted alkylene. In some embodiments, R$^5$ is an alkoxy-substituted alkylene.

R$^1$—X$^1$-groups (and optionally R$^2$—X$^2$— groups) is typically selected from H$_2$C=C(CH$_3$)C(O)—O—CH$_2$—CH(OH)—CH$_2$—O—, H$_2$C=C(CH$_3$)C(O)—O—CH$_2$—CH(O—(O)C(CH$_3$)=CH$_2$)—CH$_2$—O—, H$_2$C=C(CH$_3$)C(O)—O—CH(CH$_2$OPh)—CH$_2$—O—, H$_2$C=C(CH$_3$)C(O)—O—CH$_2$CH$_2$—N(H)—C(O)—O—CH(CH$_2$OPh)—CH$_2$—O—, H$_2$C=C(CH$_3$)C(O)—O—CH$_2$—CH(O—(O)C—N(H)—CH$_2$CH$_2$—O—(O)C(CH$_3$)C=CH$_2$)—CH$_2$—O—, H$_2$C=C(H)C(O)—O—(CH$_2$)$_4$—O—CH$_2$—CH(OH)—CH$_2$—O—, H$_2$C=C(CH$_3$)C(O)—O—CH$_2$—CH(O—(O)C—N(H)—CH$_2$CH$_2$—O—(O)C(CH$_3$)C=CH$_2$)—CH$_2$—O—, CH$_3$—(CH$_2$)$_7$ —CH(O—(O)C—N(H)—CH$_2$CH$_2$—O—(O)C(CH$_3$)C=CH$_2$)—CH$_2$—O—, H$_2$C=C(H)C(O)—O—(CH$_2$)$_4$—O—CH$_2$—CH(—O—O—(O)C(H)=CH$_2$)—CH$_2$—O— and H$_2$C=C(H)C(O)—O—CH$_2$—CH(OH)—CH$_2$—O—. H$_2$C=C(H)C(O)—O—(CH$_2$)$_4$—O—CH$_2$—CH(—O—(O)C(H)=CH$_2$)—CH$_2$—O—, and CH$_3$—(CH$_2$)$_7$ —CH(O—(O)C—N(H)—CH$_2$CH$_2$—O—(O)C(CH$_3$)C=CH$_2$)—CH$_2$—O—.

The addition-fragmentation agent may comprise a single monomer or a blend of two or more addition-fragmentation agents. The total amount of addition-fragmentation agent(s) in the filled hardenable (i.e. polymerizable) dental composition is typically no greater than 5 wt-%, or 4 wt-%, or 3 wt-%, or 2 wt-%. As the concentration of the addition-fragmentation monomer increases, the stress deflection and Watts Shrinkage typically decrease. In some embodiments, the dental compositions described herein typically exhibit a (e.g. cusp) stress deflection of no greater than 15, 14, 13, 12, 11, or 10 microns or lower. However, when the amount of addition-fragmentation agent exceeds an optimal amount, mechanical properties or depth of cure may be insufficient.

The addition-fragmentation agent is generally free-radically cleavable. Although photopolymerization is one mechanism for generating free radicals, other curing mechanisms also generate free radicals. Thus, the addition-fragmentation agent does not require irradiation with actinic radiation (e.g. photocuring) in order to provide the reduction in stress during curing.

Although low shrinkage monomers are preferred, the refractive index differential as described herein can also be utilized to improve other dental compositions having a higher shrinkage. Thus, the curable component of the curable dental composition can include a wide variety of other ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri (meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are available from a wide variety of commercial sources, such as Sigma-Aldrich, St. Louis. However, in some embodiments, the dental compositions are substantially free (less than 1, 0.5, 0.25, 0.1, or 0.005 wt.-%) of a monomer having hydroxyl groups and ethylenically unsaturated groups in a single molecule.

The dental compositions described herein may include one or more curable components in the form of ethylenically unsaturated compounds with acid functionality. Such components contain acidic groups and ethylenically unsaturated groups in a single molecule. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron. However, in some embodiments, the dental compositions are substantially free (less than 1, 0.5, 0.25, 0.1, or 0.005 wt.-%) of ethylenically unsaturated compounds with acid functionality As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates (GDMA-P), hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler.

An initiator is typically added to the mixture of polymerizable ingredients. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the mixture of monomers is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm. Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroborate. Some preferred photosensitizers may include monoketones and diketones (e.g. alpha diketones) that absorb some light within a range of about 300 nm to about 800 nm (preferably, about 400 nm to about 500 nm) such as camphorquinone, benzyl, furyl, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays or with blue light. For this embodiment, suitable photoinitiators include those available under the trade designations IRGACURE and DAROCUR from Ciba Specialty Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphine oxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-6000 mW/cm$^2$. An intensity of 1000 mW/cm$^2$ for 20 seconds can generally provide the desired cure. A variety of conventional lights for hardening such compositions can be used.

In typical embodiments, the dental composition is substantially free of a redox curing system and thus is substantially (less than 1, 0.5, 0.25, 0.1, or 0.005 wt.-%) free of polyacid and oxidizing agent. In some embodiments, the dental compositions is also free of reducing agents, as known in the art.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water. In some embodiments, the (e.g. one-part) dental compositions comprise water, typically in an amount no greater than 5 wt.-% of the total dental composition.

If desired, the compositions can contain additives such as indicators, dyes including photobleachable dyes, pigments, inhibitors, accelerators, viscosity modifiers, wetting agents, buffering agents, radical and cationic stabilizers (for example BHT,), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In other embodiments, the compositions can be hardened (e.g., polymerized) into dental articles prior to applying. For example, a dental article such as a crown may be pre-formed from the hardenable dental composition described herein. Dental composite (e.g. crowns) articles can be made from the curable composition described herein by casting the curable composition in contact with a mold and curing the composition. Alternatively, dental composite (e.g. crowns) article can be made by first curing the composition forming a mill blank and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

As used herein, "dental composition" refers to a material comprising filler capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g. one-part cements), primers (e.g., orthodontic primers), liners (applied to the base of a cavity to reduce tooth sensitivity), coatings such as sealants (e.g., pit and fissure) and varnishes; and resin restoratives (also referred to as direct composites) such as dental fillings, as well as crowns, bridges, and articles for dental implants. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein "dental article" refers to an article that can be adhered (e.g., bonded) to a tooth structure or dental implant. Dental articles include, for example, crowns, bridges, veneers, inlays, onlays, fillings, orthodontic appliances and devices.

"orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"oral surface" refers to a soft or hard surface in the oral environment. Hard surfaces typically include tooth structure including, for example, natural and artificial tooth surfaces, bone, and the like.

"hardenable" and "curable' is descriptive of a material or composition that can be cured (e.g., polymerized or cross-linked) by heating to induce polymerization and/or cross-linking; irradiating with actinic irradiation to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

"hardened" refers to a material or composition that has been cured (e.g., polymerized or crosslinked).

"hardener" refers to something that initiates hardening of a resin. A hardener may include, for example, a polymerization initiator system, a photoinitiator system, a thermal initiator and/or a redox initiator system.

"(meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

The following examples are given to illustrate, but not limit, the scope of this invention.

As used herein, all parts and percentages are by weight, all water is deionized water, and all molecular weights are average molecular weights, unless otherwise specified. Unless otherwise specified, materials can be obtained from Sigma-Aldrich, Milwaukee, WI).

Test Methods

Depth of Cure (DOC) Test Method

Depth of cure (i.e., cure depth) was determined as described in ISO 4049, using a cylindrical stainless steel curing mold as the test fixture except that the cylindrical cavity dimensions were 4 mm diameter and 20 mm depth (to accommodate greater depths of cure). In particular, the test fixture was placed on a polyester film on a flat surface and the cylindrical cavity filled with the sample to be light cured. A second polyester film placed atop the fixture and filled test fixture was pressed to provide level sample surfaces. The filled test fixture was placed on a white background surface and the composition was irradiated for 20 seconds using a dental curing light (e.g., ELIPAR FREELIGHT 2, ELIPAR S-10, or ELIPAR DEEP CURE, available from 3M Oral Care (St. Paul, MN)). After irradiation, the sample was removed from the test fixture and any uncured sample was removed within about 1 minute of irradiation (e.g., by scraping uncured material from the bottom of the sample, opposite the side irradiated with the curing light). The thickness of the remaining cured material was measured. The reported cured depths are the actual cured sample thickness in millimeters divided by 2, and are from a single measurement unless otherwise noted.

Contrast Ratio (CR) Test Method & Color Test Method

Uncured samples were formed into 1 mm thick by 30 mm diameter disks using a stainless steel mold and a Carver press (10,000 to 15,000 psi). The disks were cured by exposing the disks to illumination from an LED array (455 nm wavelength, 850 mW/cm$^2$ intensity) for 20 seconds on one side of the disk. ASTM-D2805-95 (Hiding Power of Paints by Reflectometry) was modified to measure the contrast ratio (or opacity) of the disk. Y-tristimulus values for the disks of cured composite material were measured on a Color i7 spectrophotometer (X-Rite, Grand Rapids, MI, USA) with a 25 mm aperture using separate white and black backgrounds. All measurements were made in reflection mode with a D65 Illuminant with no filters. A 10 degree angle of view was used. Contrast ratio was calculated as the ratio of the Y-tristimulus of a cured sample through a black substrate to the Y-tristimulus through the identical sample on a white substrate ($CR=R_B/R_W \times 100$) in reflectance (i.e., reflectance is defined as equal to the Y-tristimulus value). Reported contrast ratio values are from single measurements unless otherwise noted, with lower values indicative of greater translucency (i.e., transmission of light). Color data (L*a*b*) was collected on the same spectrophotometer (25 mm aperture against a white background in reflectance mode with a D65 illuminant with no filters, 10 degree angle of view, excluding specular reflection), 2-10 minutes after cure.

Refractive Index Determination

For uncured samples, refractive indices were measured with a Bausch & Lomb refractometer at 25° C., using the sodium "D" line (~589 nm).

For cured samples, refractive indices were measured as follows. The back surfaces of each sample were roughened with 1200 grit sandpaper, and then mounted on a microscope slide with double sided tape. Reflection spectral ellipsometry (RSE) data was acquired with an RC-2 ellipsometer, for incidence angles $\theta=55°\rightarrow75°$, $\Delta=10°$, $\lambda=193$ nm$\rightarrow$1000 nm. Data was analyzed for $\theta=55°\rightarrow75°$, $\Delta=10°$, $\lambda=350$ nm$\rightarrow$1000 nm. The samples were modeled as monolithic Cauchy materials.

Flexural Strength and Flexural Modulus Test Method

An uncured sample was extruded into a 2 mm×2 mm×25 mm quartz glass mold forming a test bar. The sample was then cured through the mold using 2 standard dental curing 3M ELIPAR S-10. The samples were cured by placing one light in the center of the sample bar, curing for 20 sec, then simultaneously curing the ends of the bar for 20 sec, flipping and repeating.

The samples were stored submerged in deionized water at 37° C. prior to testing (16 to 24 hrs). Flexural Strength and Flexural Modulus of the bars was measured on an Instron tester (Instron 4505 or Instron 1123, Instron Corp., Canton, Mass.) according to ANSI/ADA (American National Standard/American Dental Association) specification No. 27 (1993) at a crosshead speed of 0.75 mm/minute. The results were reported in megapascals (MPa) for flexural strength and GPa for Flexural Modulus.

Stress Test Method

To measure stress development during the curing process, a slot was machined into a rectangular 15×8×10 mm aluminum block. The slot was 8 mm long, 4 mm deep, and 4 mm across, and was located 2 mm from an edge, thus forming a 2 mm wide aluminum cusp adjacent to a 4 mm wide cavity containing dental compositions being tested. A linear variable displacement transducer (Model GT 1000, used with an E309 analog amplifier, both from RDP Electronics, United Kingdom) was positioned as shown to measure the displacement of the cusp tip as the dental composition photocured at room temperature. Prior to testing, the slot in the aluminum block was sandblasted using Rocatec Plus Special Surface Coating Blasting Material (3M Oral Care), treated with RelyX Ceramic Primer (3M Oral Care), and finally treated with a commercially available dental adhesive (e.g., Adper Easy Bond or Scotchbond Universal, each available from 3M Oral Care). A substantially similar machined aluminum block and testing apparatus are depicted FIGS. 1 and 2 of U.S. Pat. No. 9,056,043.

The slot was fully packed with the mixtures shown in the tables. The material was irradiated for 1 minute with a dental curing light (ELIPAR S-10, 3M Oral Care) positioned almost in contact (<1 mm) with the material in the slot, then the displacement of the cusp in microns was recorded 9 minutes after the light was extinguished.

Watts Shrinkage Strain Test Method

The Watts Shrinkage Strain (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. The results are reported as % shrinkage or in other words the absolute value of the decrease in volume. (5 minutes after curing)

ACTA 3 Body Wear Test Method

The ACTA 3-body wear testing for a test sample compared to FILTEK Z250 Universal Restorative (3M Oral Care) was performed substantially as described in U.S. Pat. No. 7,156,911, with the exception that the wheel was 10-slot, with sample dimensions of 15 mm length, 10 mm width, and 5 mm depth. Further detail on this method can be found by referencing: Influence of Shearing Action of Food on Contact Stress and Subsequent Wear of Stress-bearing Composites, P. Pallav, et al., Journal of Dental Research, January 1993.

Radiopacity Test Method

Radiopacity was measured using a Heliodent Plus dental X-ray device (Sirona, X-ray tube voltage: 60 kV, exposure time: 0.06 s). Radiopacity measurements are equivalent millimeters (mm) of aluminum.

Materials

Monomers of the Polymerizable Resin

"AFM-1" is an addition-fragmentation monomer which can be prepared as described in U.S. Pat. No. 9,056,043 at column 46, line 58 through column 47, line 27 ("Preparation of AFM-1");

"BisGMA" refers to 2,2-bis[4-(2-hydroxy-3-methacryloyloxypropoxy)phenyl]propane (also referred to as bisphenol A diglycidyl ether methacrylate), available from Sigma-Aldrich Corp. (St. Louis, MO);

"DDDMA" refers to 1,12-dodecanediol dimethacrylate, available under the trade designation "SR-262" from Sartomer Co., Inc. (Exton, PA);

"ERGP-IEM" refers to 2-propenoic acid, 2-methyl-, 1,1' [1,3-phenylenebis[oxy-2,1-ethanediyloxy[1-(phenoxymethyl)-2,1-ethanediyl]oxycarbonylimino-2,1-ethanediyl]]ester, which can be prepared as described at column 77, lines 33-40 of U.S. Pat. No. 8,710,113 ("Synthesis of ERGP-IEM");

"TEGDMA" refers to triethyleneglycol dimethacrylate, available from Sartomer Co., Inc. (Exton, PA);

"UDMA" refers to diurethane dimethacrylate, available under the trade designation "ROHAMERE 6661-0" from Rohm America LLC (Piscataway, NJ); also available from Dajac Laboratories (Trevose, PA);

Filler Particles

Red, yellow, and black iron oxide pigments were obtained from Elementis Pigments Inc. (East St. Louis, IL). Titanium dioxide (R690 $TiO_2$) pigment (white) was obtained from DuPont, and average particle size was measured at approximately 214 nm.

"AEROSIL R972" refers to a hydrophobic fumed silica available from Evonik (Germany);

"S/T Silica/Zirconia Clusters" refers to silane-treated silica-zirconia nanocluster filler, prepared generally as described in U.S. Pat. No. 6,730,156 at column 25, lines 50-63 (Preparatory Example A) and at column 25, line 64 through column 26, line 40 (Preparatory Example B) with minor modifications, including performing the silanization in 1-methoxy-2-propanol (rather than water) adjusted to a pH of ≠8.8 with aqueous $NH_4OH$ (rather than to a pH of 3-3.3 with trifluoroacetic acid), and obtaining the nanocluster filler by gap drying (rather than spray drying).

Nanoparticles

"S/T 20 nm Silica" refers to silane-treated silica nanoparticle filler having a nominal particle size of approximately 20 nanometers, prepared substantially as described in U.S. Pat. No. 6,572,693 at column 21, lines 63-67 ("Nanosized particle filler, Type #2");

"S/T Nanozirconia" refers to silane-treated zirconia filler, which was prepared from the zirconia sol substantially as described in U.S. Pat. No. 8,647,510 at column 36 line 61 to column 37, line 16 (Example 11A-IER). The zirconia sol was added to an equivalent weight of 1-methoxy-2-propanol containing GF-31 (1.1 mmol of GF-31 per gram of nanozirconia to be surface treated). The mixture was heated to ~85° C. for 3 hours with stirring. The mixture was cooled to 35° C., adjusted to a pH of ~9.5 with aqueous $NH_4OH$, and the mixture reheated to ~85° C. for 4 hours with stirring. The resultant material was washed with an excess of water, and t S/T Nanozirconia was isolated as a dry powder via gap drying to remove solvents. As used herein, "S/T Nanozirconia" also refers to silane-treated zirconia filler which is solvent exchanged into the resins (and pastes) without isolating the S/T Nanozirconia in dry powder form (e.g., by addition of the S/T Nanozirconia sol to a methacrylate-containing resin, followed by concentration at reduced pressure and/or heating to remove volatiles associated with the sol, as further detailed in the examples herein).

Coupling Agent/Surface Treatment

"GF-31" refers to 3-methacryloxypropyltrimethoxysilane, available from Wacker Chemie AG (Munich, Germany);

Other Components

"$YbF_3$" refers to ytterbium fluoride, approximately 100-105 nm particle size, refractive index 1.52 available from Sukgyung AT Co. Ltd., (Korea);
"BHT" refers to butylated hydroxytoluene (2,6-di-tert-butyl-4-methylphenol), available from Sigma-Aldrich Corp. (St. Louis, MO);
"BZT" refers to 2-(2'-hydroxy-5'-methacryloxyethylphenyl)-2H-benzotriazole, available from Ciba, Inc. (Tarrytown, NY) as "TINUVIN R 796", also available from Sigma-Aldrich Corp. (St. Louis, MO);
"CPQ" refers to camphorquinone;
"DPIHFP" or "DPIPF6" refers to diphenyliodonium hexafluorophosphate, available from Johnson Matthey, Alfa Aesar Division (Ward Hill, MA);
"EDMAB" refers to ethyl 4-(dimethylamino)benzoate, available from Sigma-Aldrich Corp. (St. Louis, MO);

Concentrate A (S/T Nanozirconia in BisGMA/TEGDMA)

An aqueous acetic acid-stabilized nanozirconia sol (99.9992 g, 32.68 wt. % nanozirconia with 4 wt % of the zirconia as yttria for phase stabilization, prepared as generally described in Example 11A-IER of U.S. Pat. No. 8,647,510) was combined with 1-methoxy-2-propanol (200.003 g) and GF-31 (8.741 g). After heating the mixture at 80° C. for 6 hours, a 50/50 weight mixture of BisGMA/TEGDMA (48 g) was added. The resultant mixture was concentrated by rotary evaporation under reduced pressure at ~60-85° C. to remove volatiles (e.g., water, acetic acid, 1-methoxy-2-propanol), providing Concentrate A (i.e., S/T Nanozirconia in BisGMA/TEGMA resin) as a clear, slightly opalescent liquid. Concentrate A included approximately 44.68 wt. % of S/T Nanozirconia.

Pigment Dispersion

White, Red, Black, and Yellow liquid pigment dispersions were prepared by a standard paint milling and mixing procedure through a roller mill. Table 1 is a summary of the pigment dispersions used for shading and opacification studies.

TABLE 1

| Pigment Dispersion | Pigment (wt. %) | AESROSIL R972 (wt. %) | UDMA (wt. %) |
|---|---|---|---|
| White Pigment Dispersion ("WPD") | 15 ($TiO_2$) | 10 | 75 |
| Red Pigment Dispersion ("RPD") | 5 (iron oxide) | 10 | 85 |
| Black Pigment Dispersion ("BPD") | 5 (iron oxide) | 10 | 85 |
| Yellow Pigment ("YPD") | 5 (iron oxide) | 10 | 85 |

Resins 1-4

Concentrate A was diluted by adding a mixture of 50/50 BisGMA/TEGDMA and a photoinitiator package (CPQ, EDMAB, and DPIHFP) to provide Resins 1-4. The compositions of photoinitiated Resins 1-4 are summarized in Tables 2a and 2b.

TABLE 2a

| Resin ID | S/T Nanozircoma (g) | BisGMA (g) | TEGDMA (g) | CPQ (g) | EDMAB (g) | DPIHFP (g) |
|---|---|---|---|---|---|---|
| 1 (Comparative) | 0.000 | 4.998 | 4.998 | 0.022 | 0.101 | 0.031 |
| 2 | 1.990 | 4.005 | 4.005 | 0.018 | 0.080 | 0.024 |
| 3 | 3.459 | 3.342 | 3.342 | 0.015 | 0.067 | 0.020 |
| 4 | 3.997 | 3.000 | 3.000 | 0.013 | 0.061 | 0.018 |

TABLE 2b

| Resin ID | S/T Nanozirconia (wt. %) | Effective wt % ZrO2 as oxide | BisGMA (wt. %) | TEGDMA (wt. %) | CPQ (wt. %) | EDMAB (wt. %) | DPIHFP (wt. %) |
|---|---|---|---|---|---|---|---|
| 1 | 0.000 | 0 | 49.241 | 49.241 | 0.220 | 0.994 | 0.303 |
| 2 | 19.660 | 16.560 | 39.565 | 39.565 | 0.176 | 0.794 | 0.240 |
| 3 | 33.769 | 28.443 | 32.622 | 32.622 | 0.144 | 0.652 | 0.191 |
| 4 | 39.620 | 33.372 | 29.734 | 29.734 | 0.131 | 0.603 | 0.179 |

Low Stress Resin A

Low resin A was made with 68.83 wt % ERGP-IEM, 18.77% UDMA, 8.66% DDDMA, 1.50% AFM-1, 0.30% DPIHFP, 1.1% EDMAB, 0.28% CPQ, 0.05% BHT, 0.50% BZT. This was the base resin used in fabricating Pastes 12-17, and the changes expected in the refractive index of those pastes upon curing is expected to be similar to the base resin.

Refractive index values were measured for Resins 1-4 and Resin A prior to, and after, photocuring. Measured refractive index values are summarized in Table 3.

TABLE 3

| Resin ID | Uncured Refractive Index (sodium D line ~589 nm) (absolute value of difference from filler) | Cured Refractive Index (532 nm) (absolute value of difference from filler) |
|---|---|---|
| 1 | 1.5045 (0.0335) | 1.5436 (0.0056) |
| 2 | 1.5247 (0.0133) | 1.5628 (0.0248) |
| 3 | 1.5401 (0.0021) | 1.5832 (0.0452) |
| 4 | 1.5487 (0.0107) | 1.5930 (0.0550) |
| A | 1.518 (1.515 Calculated) | 1.5417 |

After curing, polymerizable Resins 2-4 have a difference of at least 0.010.

Pastes 5-8 (Unpigmented)

Sufficient S/T Silica/Zirconia Clusters was mixed with each of Resins 1-4 to provide Pastes 5-8 respectively, with each paste having a combined S/T Nanozirconia+S/T Silica/Zirconia Cluster content of 75 wt. %. The compositions of unpigmented Pastes 5-8 are summarized in Tables 4a and 4b.

TABLE 4a

| Paste ID | Input Resin ID | Resin (g) | S/T Silica/Zirconia Clusters (g) |
|---|---|---|---|
| 5 (Comparative) | 1 | 5.002 | 15.007 |
| 6 | 2 | 6.242 | 13.753 |
| 7 | 3 | 7.490 | 12.510 |
| 8 | 4 | 8.341 | 11.666 |

TABLE 4b

| Paste ID | S/T Nanozirconia (wt. %) | Effective wt % ZrO2 as oxide | BisGMA (wt. %) | wt % TEGDMA (wt. %) | CPQ (wt. %) | wt % EDMAB (wt. %) | DPIHFP (wt. %) | S/T Silica/Zirconia Clusters (wt. %) |
|---|---|---|---|---|---|---|---|---|
| 5 (Comparative) | 0.000 | 0.000 | 12.309 | 12.309 | 0.055 | 0.249 | 0.076 | 75.002 |
| 6 | 6.137 | 5.169 | 12.351 | 12.351 | 0.055 | 0.248 | 0.075 | 68.783 |
| 7 | 12.646 | 10.652 | 12.216 | 12.216 | 0.054 | 0.244 | 0.072 | 62.552 |
| 8 | 16.518 | 13.913 | 12.396 | 12.396 | 0.055 | 0.251 | 0.075 | 58.309 |

Contrast ratio and depth of cure measurements for each of photocured Pastes 5-8 are summarized in Table 5. Table 5 shows that the contrast ratio of the cured disks increases with increasing refractive index mismatch between: (i) the refractive index of the S/T Silica/Zirconia Clusters and (ii) the combined refractive index of the resin and S/T Nanozirconia mixture.

TABLE 5

| Paste ID | Contrast Ratio (cured) | Depth of Cure (mm)[¥] | L* | a* | b* |
|---|---|---|---|---|---|
| 5 | 29.6 | 7.8 ± .07 | 89.99 | −0.985 | 5.31 |
| 6 | 50.6 | 5.9 ± 0.08 | 90.145 | −1.08 | 5.57 |
| 7 | 62.1 | 4.2 ± 0.19 | 93.53 | −1.095 | 6.08 |
| 8 | 66.4 | 3.8 ± 0.07 | 93.65 | −0.995 | 5.84 |

[¥]ELIPAR S-10
Pastes 5-8 meet the ISO 4049 standard.

Comparative Pastes 9-11 (White Pigmented, S/T Nanozirconia-Free)

A duplicate (larger) batch of Resin 1 was made (no nanozirconia) by taking a 250 g of a 50/50 weight % blend of BisGMA and TEGDMA and adding to it 0.549 g CPQ, 2.499 g EDMAB and 0.748 g DPIFHP. From this resin pastes with 75 wt % S/T Silica/Zirconia Clusters and 25 weight % initiated resin were made and pigmented with the White Pigment Dispersion liquid white pigment to approximate the contrast ratios of Pastes 5-8. Compositions of the pigmented pastes are listed below:

TABLE 6a

| Paste ID | Resin (g) | S/T Silica/Zirconia Clusters (g) | WPD (g) |
|---|---|---|---|
| 9 | 2.354 | 8.017 | 0.034 |
| 10 | 2.230 | 7.991 | 0.022 |
| 11 | 2.117 | 8.003 | 0.011 |

TABLE 6b

| Paste ID | BisGMA (wt. %) | TEGDMA (wt. %) | CPQ (wt. %) | EDMAB (wt. %) | DPIHFP (wt. %) | S/T Silica/Zirconia Clusters (wt. %) | WPD* (wt. %) |
|---|---|---|---|---|---|---|---|
| 9 | 11.142 | 11.142 | 0.050 | 0.225 | 0.069 | 77.050 | 0.323 (0.0485) |
| 10 | 10.721 | 10.721 | 0.048 | 0.216 | 0.066 | 78.009 | 0.218 (0.0327) |
| 11 | 10.288 | 10.288 | 0.046 | 0.208 | 0.063 | 78.995 | 0.112 (0.0168) |

*As reported in Table 1, the concentration of pigment is 15% of the amount of the dispersion. The amount of pigment is reported in parenthesis below the amount of the dispersion.

Contrast ratio and ISO 4049 depth of cure was measured for each of pastes 9-11 and comparative paste 18 as reported in the following Table 7:

TABLE 7

| Paste ID | Contrast Ratio (opacity) | Depth of Cure (mm)[¥] | L* | a* | b* |
|---|---|---|---|---|---|
| 9 | 63.3 | 4.00 ± .01 | 94.195 | −1.575 | 7.335 |
| 10 | 54.4 | 4.8 ± .18 | 93.63 | −1.71 | 7.585 |
| 11 | 46.7 | 5.7 ± .09 | 92.82 | −1.735 | 7.145 |
| 18 | 52.4 | 4.8 ± .10 | 90.02 | −1.63 | 14.08 |

[¥]ELIPAR S-10
Pastes 9-11 and 18 meet the ISO 4049 standard.

Pastes 12-17

Pastes 12-17 were made from all dry-powder ingredients, and resins more suited toward bulk fill applications (lower stress) demonstrating a more manufacturing-friendly method of achieving the same effect. These were made using a speed mixer (SPEEDMIXER available from Flacktek, Inc., Landrum, SC). All the components were mixed together as a one-part system. The concentration of components in grams is reported in Tables 8a and 8b. The concentration of components in wt.-% is reported in Tables 9a and 9b. Note that paste 15 uses much less white pigment. Paste 17 cures deeply, but has a low contrast ratio.

TABLE 8a

| Paste ID | ERGP-IEM (g) | UDMA (g) | DDDMA (g) | AFM-1 (g) | S/T Nanozirconia (g) | S/T 20 nm Silica (g) | YbF$_3$ (g) | S/T Silica/Zircornia Clusters (g) |
|---|---|---|---|---|---|---|---|---|
| 12 | 3.341 | 0.911 | 0.421 | 0.073 | 0.327 | 0.608 | 1.169 | 13.477 |
| 13 | 2.753 | 0.751 | 0.347 | 0.060 | 0.000 | 2.678 | 0.000 | 10.714 |
| 14 | 2.705 | 0.738 | 0.341 | 0.059 | 1.541 | 0.514 | 0.000 | 10.787 |
| 15 | 2.616 | 0.713 | 0.329 | 0.057 | 0.835 | 0.681 | 0.681 | 10.607 |
| 16 | 5.985 | 1.632 | 0.753 | 0.130 | 1.836 | 0.768 | 1.531 | 26.439 |
| 17 | 1.643 | 0.448 | 0.207 | 0.036 | 0.160 | 0.297 | 0.571 | 6.585 |

TABLE 8b

| Paste ID | BPD (g) | RPD (g) | YPD (g) | WPD (g) | CPQ (g) | EDMAB (g) | DPIHFP (g) | BHT (g) | BZT (g) |
|---|---|---|---|---|---|---|---|---|---|
| 12 | 0.001 | 0.003 | 0.018 | 0.044 | 0.014 | 0.053 | 0.015 | 0.002 | 0.024 |
| 13 | 0.003 | 0.002 | 0.017 | 0.005 | 0.011 | 0.044 | 0.012 | 0.002 | 0.020 |
| 14 | 0.002 | 0.002 | 0.017 | 0.000 | 0.011 | 0.043 | 0.012 | 0.002 | 0.020 |
| 15 | 0.000 | 0.000 | 0.000 | 0.000 | 0.011 | 0.042 | 0.011 | 0.002 | 0.019 |
| 16 | 0.001 | 0.005 | 0.017 | 0.006 | 0.026 | 0.096 | 0.024 | 0.004 | 0.044 |
| 17 | 0.000 | 0.000 | 0.000 | 0.000 | 0.007 | 0.026 | 0.007 | 0.001 | 0.012 |

TABLE 9a

| Paste ID | ERGP-IEM (wt. %) | UDMA (wt. %) | DDDMA (wt. %) | AFM-1 (wt. %) | S/T Nanozircornia (wt. %) | Effective wt % ZrO2 as oxide | S/T 20 nm Silica (wt. %) | YbF$_3$ (wt. %) | S/T Silica/Zirconia Clusters (wt. %) |
|---|---|---|---|---|---|---|---|---|---|
| 12 | 16.29 | 4.44 | 2.05 | 0.36 | 1.60 | 1.35 | 2.97 | 5.70 | 65.74 |
| 13 | 15.81 | 4.31 | 1.99 | 0.34 | 0.00 | 0.00 | 15.37 | 0.00 | 61.51 |
| 14 | 16.11 | 4.39 | 2.03 | 0.35 | 9.18 | 7.73 | 3.06 | 0.00 | 64.23 |
| 15 | 15.75 | 4.30 | 1.98 | 0.34 | 5.03 | 4.24 | 4.10 | 4.10 | 63.88 |
| 16 | 15.23 | 4.15 | 1.92 | 0.33 | 4.67 | 3.93 | 1.95 | 3.90 | 67.28 |
| 17 | 16.43 | 4.48 | 2.07 | 0.36 | 1.60 | 1.35 | 2.97 | 5.71 | 65.85 |

TABLE 9b

| Paste ID | BPD (wt. %) | RPD (wt. %) | YPD (wt. %) | WPD (wt. %) | CPQ (wt. %) | EDMAB (wt. %) | DPIHFP (wt. %) | BHT (wt. %) | BZT (wt. %) |
|---|---|---|---|---|---|---|---|---|---|
| 12 | 0.01 (0.0005) | 0.01 (0.0005) | 0.09 (0.0045) | 0.22 (0.033) | 0.07 | 0.26 | 0.07 | 0.01 | 0.12 |
| 13 | 0.01 (0.0005) | 0.01 (0.0005) | 0.10 (0.005) | 0.03 (0.0045) | 0.06 | 0.25 | 0.07 | 0.01 | 0.11 |
| 14 | 0.01 (0.0005) | 0.01 (0.0005) | 0.10 (0.005) | 0.00 | 0.07 | 0.26 | 0.07 | 0.01 | 0.12 |
| 15 | 0.00 | 0.00 | 0.00 | 0.00 | 0.06 | 0.25 | 0.07 | 0.01 | 0.11 |
| 16 | 0.00 | 0.01 (0.0005) | 0.04 (0.002) | 0.01 (0.0015) | 0.07 | 0.24 | 0.06 | 0.01 | 0.11 |
| 17 | 0.00 | 0.00 | 0.00 | 0.00 | 0.07 | 0.26 | 0.07 | 0.01 | 0.12 |

*As reported in Table 1, the concentration of pigment is 15% in the case of WPD and 5% for RPD, BPD, and YPD of the amount of the dispersion. The amount of pigment is reported in parenthesis below the amount of the dispersion.

The measured contrast ratio and cure depths for pastes 12-17 were:

TABLE 10

| Paste ID | Depth of Cure (mm)$^¥$ | **Calculated refractive index of uncured resin, cured resin (absolute value of difference from filler) | Contrast Ratio (cured) | L* | a* | b* |
|---|---|---|---|---|---|---|
| 12 | 2.99 ± 0.03 | 1.515, 1.545 (0.023/0.007) | 57.26 | 84.23 | 6.41 | 28.14 |
| 13 | 3.15 ± 0.01 | 1.499, 1.529 (0.039/0.009) | 55.66 | 82.85 | 5.00 | 27.69 |
| 14 | 3.31 ± 0.01 | 1.531, 1.561 (0.007/0.013) | 58.68 | 82.18 | 5.26 | 28.48 |
| 15 | 4.62 ± 0.05 | 1.521, 1.551 (0.017/0.023) | 44.50 | N/A | N/A | 8.9 |
| 16 | 4.14 ± .17 | 1.524, 1.554 (0.014/0.016) | 49.03 | 84.06 | 3.75 | 22.04 |
| 17 | 5.70 ± .37 | 1.515/1.545 (0.023/0.003) | 34.60 | 88.30 | −1.73 | 7.13 |

$^¥$ELIPAR DEEP CURE or FREELIGHT 2
**The calculated and cured resin values are inclusive of the nanoparticles.

Pastes 12, 13, 14, and 16 are pigmented. When comparing pastes 12 and 14, for example, there is a significant increase in the cure depth that can be achieved through the incorporation of higher levels of the S/T Nanozirconia. The resin is estimated to shift upwards in refractive index 0.03-0.04 units upon cure, based upon Resins 1-4, with some dependence on the inherent shrinkage of the resin upon cure. Pastes 15 and 17 have no pigmentation, and a contrast ratio of only 34 for the lower index material in Paste 17 is necessary to achieve a high cure depth in the comparative example, so will be more lacking in aesthetics. Paste 15 gives a higher contrast ratio without pigmentation than paste 17 with a cure depth of over 4.5 mm. Paste 16 is was pigmented fully to an A3 shade with a 49 contrast ratio (acceptable in many restorations), and has a cure depth in excess 4 mm due to the need for lesser pigmentation to achieve the desired contrast ratio for the final cured material.

Paste 18

A commercially available bulk cure flowable composite (Paste 18) was analyzed and tested. The composition of the commercially available composite included barium glass, ytterbium trifluoride and copolymers with a filler loading of 71 wt.-% and an inorganic content of 68.2 wt. %. The filler particles had a particle size ranging from 0.1 to 30 microns with an average particle size of 5 microns. The resin contained a mixture of BisGMA (~19%), ethoxylated bisphenol A dimethacrylate (~69%), dimethyloltricyclodecane dimethacrylate (~11%), +"other ingredients", presumed to be initiator and pigments.

Mechanical Properties Testing

Pastes 16, 17 and 18 were tested for mechanical properties of flexural strength and modulus, 3-body wear resistance, Watts shrinkage strain, x-ray radiopacity and cusp deflection.

TABLE 11

| Paste | Flexural Strength (MPa) | Flexural Modulus (GPa) | 3-body wear (xZ250 rate) | Cusp Deflection, 4 mm (microns) | Watts shrinkage strain (%) | Radiopacity (equivalent mm of aluminum) |
|---|---|---|---|---|---|---|
| 16 | 151 ± 7 | 10.1 ± .3 | 0.94 ± 0.10 | 10.07 ± .37 | 1.76 ± .04 | 3.10 ± .08 |
| 17 | 141 ± 15 | 11.0 ± .3 | 0.73 ± 0.06 | 10.81 ± .20 | 1.73 ± .06 | 3.07 ± .03 |
| 18 | 109 ± 5 | 7.0 ± .2 | 2.38 ± 0.24 | 8.70 ± .38 | 2.34 ± .03 | 2.68 ± .11 |

As can be seen, the strength, radiopacity, wear rate, and shrinkage of Pastes 16 and 17 are improved over commercially available Paste 18.

Pastes 19-25

Pastes 21-25 were made from two "stock" pastes (paste 19, pigmented with RPD and WPD only; paste 20, pigmented with RPD only) that were made from all dry-powder ingredients, and resins more suited toward bulk fill applications (lower stress) demonstrating a simple laboratory method of investigating contrast ratio and depth of cure effects on a set formulation with varying WPD content. Total resin, filler, and pigment components were set as shown in Table 12a, reported as percent composition by weight. These stock pastes are useful because they can be pigmented to multiple shades with acceptable contrast ratio, and at least 3.5 mm depth of cure, due to their having an optimized nanozirconia content. Pastes 21-25 were made from stock pastes 19 and 20 by mixing the reported weights of pastes 19 and 20, shown in Table 12b. These were all made using a speed mixer (SPEEDMIXER available from Flacktek, Inc., Landrum, SC). All the components were mixed together as a one-part system. Table 12b clearly shows that, given the right base formulation, a depth of cure of 3.5 mm and a contrast ratio of 60 can be achieved using 0.045 wt. % white pigment.

TABLE 12a

| Paste ID | Resin* (wt. %) | S/T Nano-zirconia (wt. %) | S/T 20 nm Silica (wt. %) | YbF$_3$ (wt. %) | S/T Silica/Zirconia Clusters (wt. %) | RPD (wt. %) | WPD (wt. %) |
|---|---|---|---|---|---|---|---|
| 19 | 23.528 | 4.692 | 1.782 | 4.189 | 65.504 | 0.005 | 0.300 |
| 20 | 23.599 | 4.706 | 1.788 | 4.202 | 65.701 | 0.005 | 0.000 |

*Resin contents by wt. %: ERGP-IEM 68.83, UDMA 18.77 DDDMA 8.66, AFM-1 1.50, EDMAB 1.10, DPIHFP 0.30, CPQ 0.28, BHT 0.05, BZT 0.50.

TABLE 12b

| Paste ID | Paste 19 (g) | Paste 20 (g) | Calculated RPD (wt. %) | Calculated WPD (wt. %) | Calculated Red Pigment (wt. %) | Calculated White Pigment (wt. %) | Contrast Ratio (Cured) | Depth of Cure (mm)** |
|---|---|---|---|---|---|---|---|---|
| 21 | 20.00 | 0.00 | 0.005 | 0.30 | 0.00025 | 0.045 | 60.39 | 3.54 ± 0.06 |
| 22 | 16.68 | 3.33 | 0.005 | 0.25 | 0.00025 | 0.038 | 58.51 | 3.68 ± 0.07 |
| 23 | 13.30 | 6.68 | 0.005 | 0.20 | 0.00025 | 0.030 | 56.44 | 3.74 ± 0.09 |
| 24 | 10.00 | 10.00 | 0.005 | 0.15 | 0.00025 | 0.023 | 54.10 | 4.10 ± 0.01 |
| 25 | 6.66 | 13.29 | 0.005 | 0.10 | 0.00025 | 0.015 | 51.21 | 4.40 ± 0.08 |

**Elipar Deep Cure S, 20 second curing time

What is claimed is:
1. A dental composition comprising:
a polymerizable resin comprising:
  a homogenous organic phase comprising:
    one or more addition-fragmentation material represented by Formulae I:

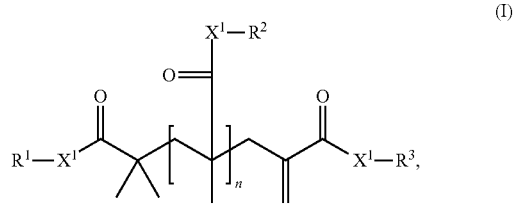

(I)

wherein:
$R^1$, $R^2$, and $R^3$ are independently Z—Y—, a (hetero) alkyl group, or a (hetero)aryl group, with the proviso that at least one of $R^1$, $R^2$ and $R^3$ is Z—Y—,
each $X^1$ is independently —O— or —NR$^4$—,
each Z is independently

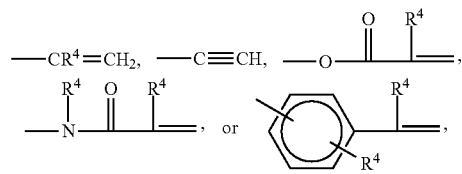

each Y is independently —R$^5$—, —C(O)—O—R$^6$—, —C(O)—NR$^4$—R$^6$—, —R$^6$—C(O)—O—R$^6$—, —O—R$^6$—, —S—R$^6$—, —NR$^4$—R$^6$—, —SO$_2$—R$^6$—, —C(O)—R$^6$—, —OC(O)—R$^6$—, or —NR$^4$—C(O)—R$^6$—,
each $R^4$ is independently —H or C$_{1-4}$ alkyl,
each $R^5$ is independently C$_{1-10}$ alkylene optionally substituted with hydroxyl or alkoxy,
each $R^6$ is independently C$_{1-6}$ alkylene, 5- or 6-membered cycloalkylene, or
C$_{6-16}$ arylene,
n is 0 or 1,
one or more low shrinkage monomer represented by the Formulae II:

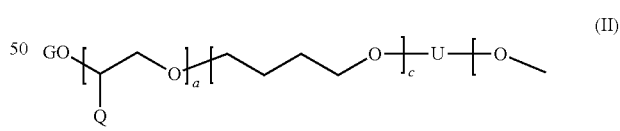

(II)

-continued

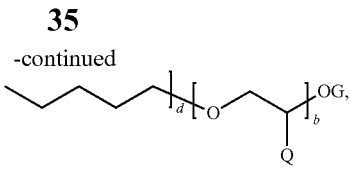

wherein:
each G is independently selected from:

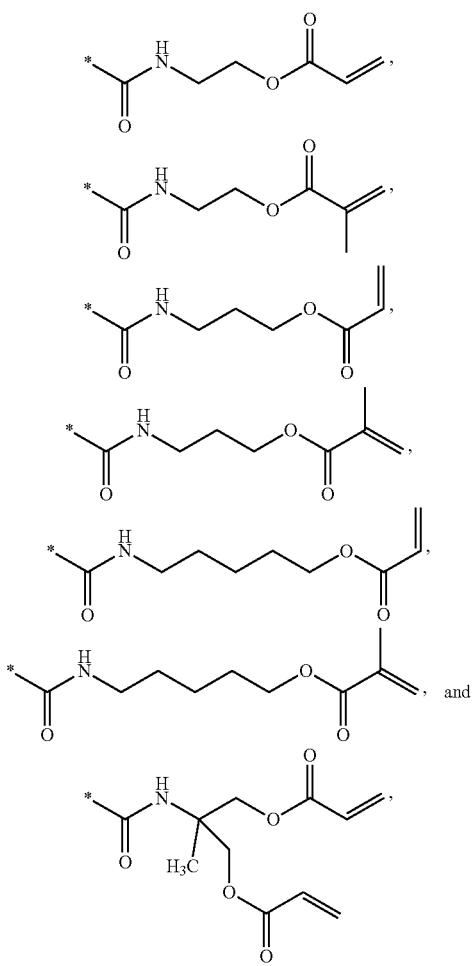

each Q is independently hydrogen, methyl, phenyl, and phenoxymethyl,
U is selected from:

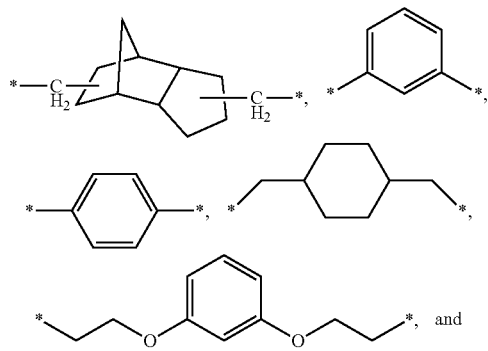

-continued

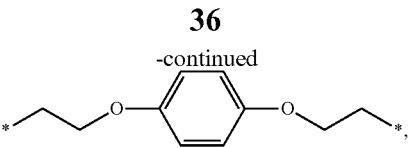

each of a, b, c, and d is an integer independently selected from 0-3, wherein a+b=1-6, and c+d=1-6, and one or more low viscosity polymerizable diluent characterized by a viscosity of no greater than 300 Pa*s, and nanoparticles having a refractive index of at least 1.600 and an average discrete or aggregate particle size of no greater than 100 nm; and inorganic metal oxide filler characterized by a discrete or aggregate average particle size of at least 200 nm;

wherein the nanoparticles are present at a concentration to provide a refractive index differential between the polymerizable resin in a cured state and the inorganic metal oxide filler such that the contrast ratio of the dental composition is at least 40.

2. A method of treating a tooth surface, the method comprising:
providing a dental composition according to claim 1;
placing the dental composition on a tooth surface in the mouth of a subject; and
curing the polymerizable resin thereby hardening the dental composition.

3. A dental article comprising the dental composition of claim 1, wherein the dental composition is at least partially hardened.

4. The dental composition of claim 1, the addition-fragmentation material represented by Formula Ia:

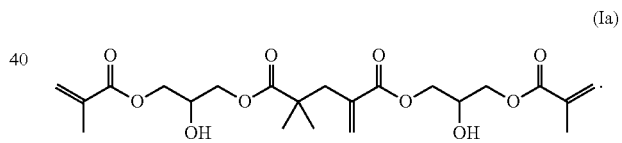

5. The dental composition of claim 1, the one or more addition-fragmentation material present in the dental composition in an amount of no greater than 2 wt %.

6. The dental composition of claim 1, the one or more low shrinkage monomer being present within the homogenous organic phase in an amount of 50-70 wt %.

7. The dental composition of claim 1, the one or more low shrinkage monomer being present within the dental composition in an amount 15-20 wt %.

8. The dental composition of claim 1, one or more low shrinkage monomer represented by Formulae IIa:

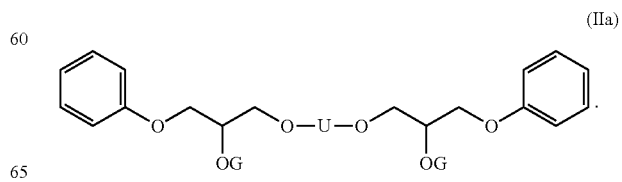

9. The dental composition of claim 8, wherein each G is

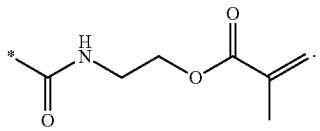 [SMILES: *C(=O)NCCOC(=O)C(=C)C]

10. The dental composition of claim 1, comprising a low shrinkage monomer represented by formula IIb:

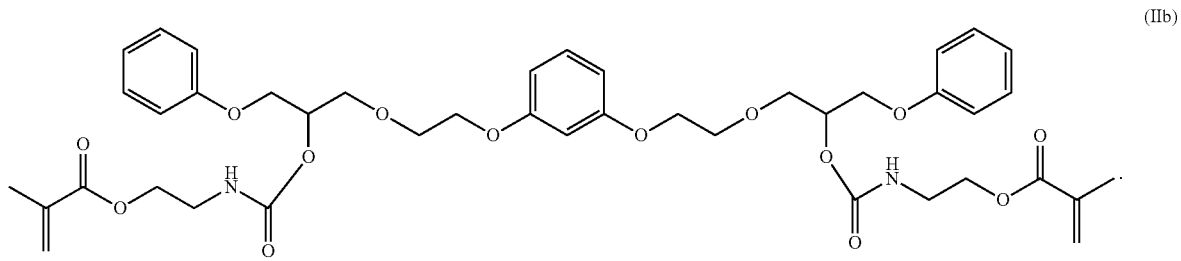 [SMILES: C=C(C)C(=O)OCCNC(=O)OC(COCCOc1cccc(OCCOCC(COc2ccccc2)OC(=O)NCCOC(=O)C(=C)C)c1)COc1ccccc1]

(IIb)

11. The dental composition of claim 10, the low shrinkage monomer of Formula III being present within the homogenous organic phase in an amount of 50-70 wt %.

12. The dental composition of claim 10, the low shrinkage monomer of Formula III being present within the dental composition in an amount of 15-20 wt %.

13. The dental composition of claim 1, the one or more low viscosity polymerizable diluent present in the dental composition in an amount of 2-10 wt %.

14. The dental composition of claim 1, the one or more low viscosity polymerizable diluent selected from 1,12-dodecanediol dimethacrylate (DDDMA), urethane dimethacrylate (UDMA), triethylene glycol dimethacrylate (TEGDMA), glycerol dimethacrylate (GDMA), ethyleneglycol dimethacrylate, neopentylglycol dimethacrylate (NPGDMA), polyethyleneglycol dimethacrylate (PEGDMA), and a combination thereof.

15. The dental composition of claim 1, comprising low viscosity polymerizable diluents of formula III and formula IV:

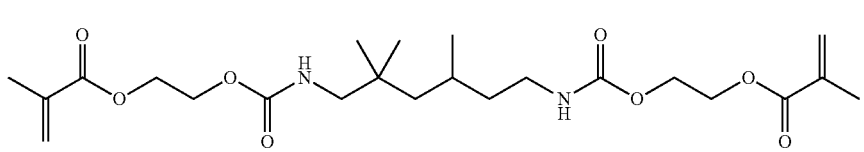

(UMDA, III)

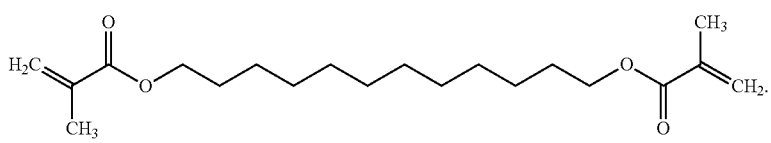

(DDDMA, IV)

16. The dental composition of claim 1, one or more of:
the nanoparticles comprising silica nanoparticles, zirconia nanoparticles, or a combination thereof, and
the inorganic metal oxide filler comprising silica particles, zirconia particles, or a combination thereof.

17. The dental composition of claim 16, the silica nanoparticles present in the dental composition in an amount no greater than 5 wt %, and the silica nanoparticles and the zirconia nanoparticles present in a weight ratio of 1:1 to 1:10.

18. The dental composition of claim 1, the inorganic metal oxide filler being present in the dental composition in an amount of 60-70 wt %.

19. The dental composition of claim 1, the inorganic metal oxide filler comprising silica particles, zirconia particles, or a combination thereof.

20. The dental composition of claim 1, further comprising one or more:
- a photoinitiator system,
- one or more pigment, and
- yitterbium fluoride.

* * * * *